(12) United States Patent
Cline et al.

(10) Patent No.: US 8,131,476 B2
(45) Date of Patent: Mar. 6, 2012

(54) SYSTEM AND METHOD FOR CO-REGISTERING MULTI-CHANNEL IMAGES OF A TISSUE MICRO ARRAY

(75) Inventors: Harvey Ellis Cline, Schenectady, NY (US); Ali Can, Troy, NY (US)

(73) Assignee: General Electric Company, Niskayuna, NY (US)

( * ) Notice: Subject to any disclaimer, the term of this patent is extended or adjusted under 35 U.S.C. 154(b) by 1080 days.

(21) Appl. No.: 11/500,028

(22) Filed: Aug. 7, 2006

(65) Prior Publication Data
US 2008/0032328 A1 Feb. 7, 2008

(51) Int. Cl.
*G01N 33/48* (2006.01)
(52) U.S. Cl. .......... 702/19; 382/133; 382/165; 382/173; 382/283; 530/350; 536/23.1; 703/2; 703/11; 435/6; 435/7.1; 436/64
(58) Field of Classification Search .................. None
See application file for complete search history.

(56) References Cited

U.S. PATENT DOCUMENTS

| | | | |
|---|---|---|---|
| 5,888,743 A | 3/1999 | Das | |
| 5,995,645 A | 11/1999 | Soenksen et al. | |
| 6,150,173 A | 11/2000 | Schubert | |
| 6,160,617 A | 12/2000 | Yang | |
| 6,195,451 B1 | 2/2001 | Kerschmann et al. | |
| 6,573,043 B1 | 6/2003 | Cohen et al. | |
| 6,788,816 B1 | 9/2004 | Kiyuna | |
| 6,995,020 B2 | 2/2006 | Capiodieci et al. | |
| 7,219,016 B2 | 5/2007 | Rimm et al. | |
| 7,321,881 B2 | 1/2008 | Saidi et al. | |
| 7,467,119 B2 | 12/2008 | Saidi et al. | |
| 7,483,554 B2 | 1/2009 | Kotsianti et al. | |
| 7,505,948 B2 | 3/2009 | Saidi et al. | |
| 7,709,222 B2 | 5/2010 | Rimm et al. | |
| 2002/0076092 A1 | 6/2002 | Ellis et al. | |
| 2002/0164063 A1 | 11/2002 | Heckman | |
| 2002/0177149 A1 | 11/2002 | Rimm et al. | |
| 2002/0187487 A1 | 12/2002 | Goldenring et al. | |
| 2003/0036855 A1 | 2/2003 | Harris et al. | |
| 2003/0077675 A1 | 4/2003 | Das | |
| 2003/0184730 A1* | 10/2003 | Price | 356/39 |
| 2004/0023320 A1 | 2/2004 | Steiner et al. | |
| 2004/0029213 A1* | 2/2004 | Callahan et al. | 435/40.5 |
| 2004/0197839 A1 | 10/2004 | Daniely et al. | |
| 2004/0248325 A1 | 12/2004 | Bukusoglul | |
| 2005/0267690 A1* | 12/2005 | Cong et al. | 702/19 |
| 2006/0094868 A1 | 5/2006 | Giuliano et al. | |
| 2007/0016373 A1 | 1/2007 | Hunter et al. | |
| 2007/0099219 A1 | 5/2007 | Teverovskiy et al. | |
| 2007/0111251 A1 | 5/2007 | Rosania et al. | |
| 2008/0118916 A1 | 5/2008 | Sood et al. | |
| 2008/0118934 A1 | 5/2008 | Gerdes et al. | |
| 2008/0118944 A1 | 5/2008 | Larsen et al. | |
| 2008/0144895 A1 | 6/2008 | Hunter et al. | |
| 2010/0062452 A1 | 3/2010 | Gustavson et al. | |

FOREIGN PATENT DOCUMENTS

| | | |
|---|---|---|
| EP | 0345953 B1 | 7/1994 |
| EP | 1416278 B1 | 11/2004 |
| WO | 02086498 A1 | 10/2002 |
| WO | WO2004038418 A1 | 5/2004 |
| WO | WO2006016697 A1 | 2/2006 |
| WO | 2007130677 A2 | 11/2007 |
| WO | 2007136724 A2 | 11/2007 |
| WO | 2008064067 A2 | 5/2008 |
| WO | 2008133727 A2 | 11/2008 |
| WO | 2008133728 A2 | 11/2008 |
| WO | 2008133729 A2 | 11/2008 |

OTHER PUBLICATIONS

Camp, R., "Automated Subcellular Localization and Quantification of Protein Expression in Tissue Microarrays", Nature Medicine, vol. 8, No. 11, Nov. 1, 2002, pp. 1323-1327.
Resnick, M., "Epidermal Growth Factor Receptor, c-MET, beta-catenin, and p53 Expression as Prognostic Indicators in Stage II Colon Cancer, A Tissue Microarray Study", Journal of the American Assoc. for Cancer Research, May 1, 2004, vol. 10, No. 9, pp. 3069-3075.
PCT Search Report—Jan. 23, 2009.
T Hothorn and B. Lausen, "On the exact distribution of maximally selected rank statistics", Computational Statistics & Data Analysis, 2003, pp. 121-137, vol. 43.
Rom T. Altstock, et al., "Algorithms for Quantitation of Protein Expression Variation in Normal Versus Tumor Tissue as a Prognostic Factor in Cancer: Met Oncogene Expression, and Breast Cancer as a Model", Cytometry, Jul. 20, 2000, pp. 155-165, vol. 41.
Robert L. Camp et al., "Automated subcellular localization and quantification of protein expression in tissue microarrays", Nature Medicine, Nov. 2002, pp. 1323-1328, vol. 8, No. 11. K. Martin Hoffman, et al., "Gastrointestinal Hormones Cause Rapid c-Met Receptor Down-regulation by a Novel Mechanism Involving Clathrin-mediated Endocytosis and a Lysosome-dependent Mechanism", Journal of Biological Chemistry, Dec. 8, 2006, pp. 37705-37719, vol. 281, No. 49.
Gagani Athauda et al, "c-Met Ectodomain Shedding Rate Correlates with Malignant Potential", Clin Cancer Res, Jul. 15, 2006, pp. 4154-4162, vol. 12, No. 14.
S. Kermorgant et al., "c-Met Signalling: Spatio-Temporal Decisions", Cell Cycle, Mar. 2005, pp. 352-355, vol. 4, Issue 3.
Wolfgang Hilbe, et al., "Comparison of automated cellular imaging system and manual microscopy for immunohistochemically stained cryostat sections of lung cancer specimens applying p53, Ki-67 and p120", Oncology Reports, May 13, 2003, pp. 15-20, vol. 10.
James D. Cowan et al., "Cruella, Develop mg a Scalable T ssue M Croarray Data Management System", Arch Pathol Lab Med, Jun. 2006, pp. 817-822, vol. 130.

(Continued)

*Primary Examiner* — Carolyn L. Smith
(74) *Attorney, Agent, or Firm* — Jenifer E. Haeckl

(57) ABSTRACT

A system and methods for co-registering multi-channel images of a tissue micro array, comprising the steps of, providing a biological material on a substrate; applying one or more molecular probes, adapted to provide fluorescent molecular markers, to the biological material; obtaining a first digital image of the biological material and the fluorescent molecular markers; applying a morphological stain to the biological material; obtaining a second digital image of the biological material, computing information common to the first and second images; and co-registering the second image with the first image based on one or more registration metrics.

24 Claims, 4 Drawing Sheets

OTHER PUBLICATIONS

Figure 1A:
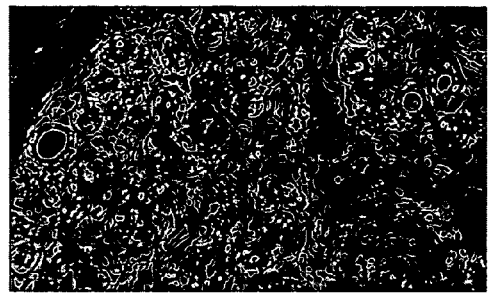

Michael Mengel, M.D., et al., "Standardized On-Slide Control for Quality Assurance in the Immunohistochemical Assessment of Therapeutic Target Molecules in Breast Cancer", The Breast Journal, 2005, pp. 34-40, vol. 11, No. 1.

Cesar Eguiluz, et al., "Multitissue array review: A chronological description of tissue array techniques, applications and procedures", Pathology-Research and Practice, 2006, pp. 561-568, vol. 202.

J.B. Antoine Maintz and Max A. Viergever, "A Survey of Medical Image Registration", Medical Image Analysis, 1998, pp. 1-37, vol. 2, No. 1.

Ashburner et al, "Unified Segmentation", Academic Press, vol. 26, No. 3, Jul. 1, 2005, pp. 839-851.

Debruijne et al., "Multi-object Segmentation Using Shape Particles", Information Processing in Medical Imaging; vol. 3565. Jul. 10, 2005, pp. 762-773.

PCT Search Report & Written Opinion—Mar. 27, 2009.

Thevenaz, Optimization of Mutual Information for Multiresolution Image Registration, *IEEE Transactions on Image Processing*, vol. 9, No. 12, pp. 2083-2099, Dec. 2000.

Rodenacker, et al, A Feature Set for Cytometry on Digitized Microscopic Images, *Analytical Cellular Pathology*, 25, pp. 1-36, 2003.

Erlandsson, et al., Abnormal Expression Pattern of Cyclin E in Tumor Cells, *Int. J. Cancer*, 104, pp. 369-375, 2003.

Van Vlierberghe, et al., Four-Color Staining Combining Fluorescence and Brightfield Microscopy for Simultaneous Immune Cell Phenotyping and Localization in Tumor Tissue Sections, *Microscopy Research and Technique*, 67, pp. 15-21, 2005.

Lindblad, et al., Image Analysis for Automatic Segmentation of Cytoplasms and Classification of Rac1 Activation, *Cytometry Part A*, 57A, pp. 22-33, 2004.

Gerstner, et al., Quantitative Histology by Multicolor Slide-Based Cytometry, *Cytometry Part A*, 59A, pp. 210-219, 2004.

Wahlby, et al., Sequential Immunofluorescence Staining and Image Analysis for Detection of Large Numbers of Antigens in Individual Cell Nuclei, *Cytometry*, 47, pp. 32-41, 2002.

Hermiston, et al., Simultaneous Localization of Six Antigens in Single Sections of Transgenic Mouse Intestine Using a Combination of Light and Fluorescence Microscopy, *The Journal of Histochemistry and Cytochemistry*, vol. 40, No. 9, pp. 1283-1290, 1992.

Wahlby, et al., Algorithms for Cytoplasm Segmentation of Fluorescence Labelled Cells, *Analytical Cellular Pathology*, 24, pp. 101-111, 2002.

PCT/US2007/074380, PCT Search Report, Jun. 2, 2009.

W. Chen et al., "A Prototype for Unsupervised analysis of Tissue Microarrays for Cancer Research and Diagnostics," IEEE Transactions on Information Technology in Biomedicine, vol. 8, No. 2, Jun. 2004. pp. 89-96.

P. Capodieci et al., "Gene expression profiling in single cells within tissue," 2005 Nature Publishing Group, vol. 2, No. 9, Sep. 2005, pp. 663-665.

W. Schubert et al., : Analyzing proteome topology and function by automated multidimensional fluorescence microscopy, 2006 Nature Publishing Group, http://www.nature.com/naturebiotechnology, Oct. 2006, pp. 1-11.

W. Schubert, "Exploring Molecular Networks Directly in the Cell," 2006 International Society of Analytical Cytology, Cytometry Part A, vol. 69A, 2006, pp. 109-112.

R. F. Murphy, "A combination of microscope technology and statistical analysis enables the identification of proteins that share subcellular location patterns," 2006 Nature Publishing Group, Nature Biotechnology, vol. 24, No. 10, Oct. 2006, pp. 1223-1224.

T. W. Nattkemper et al., "Human vs. machine: evaluation of fluorescence micrographs," Pergamon, Computers in Biology and Medicine, Computers in Biology and Medicine, vol. 33, 2003, pp. 31-43.

T. W. Nattkemper et al., "A hybrid system for cell detection in digital micrographs," Paper presented @ Biomedical Engineering Conference, Feb. 16-18, 2004, 4 pages.

T.W. Nattkemper et al., "A Neural Network Architecture for Automatic Segmentation of Fluorescence Micrographs," ESANN' 2000 proceedings—European Symposium on Artificial Neural Networks, (Belgium), Apr. 26-28, 2000, ISBN 2-930307-00-5, pp. 177-182.

A. V. Kuznetsov et al., "Functional Imaging of Mitochondria in Saponin-permeabilized Mice Muscle Fibers," The Journal of Cell Biology, vol. 140, No. 5, Mar. 9, 1998, pp. 1091-1099.

K. Rodenacker et al., "A feature set for cytometry on digitized microscopic images," Analytical Cellular Pathology, vol. 25, 2003, pp. 1-36.

JP2001092980 Abstract, Apr. 6, 2011.

* cited by examiner

SYSTEM AND METHOD FOR CO-REGISTERING MULTI-CHANNEL IMAGES OF A TISSUE MICRO ARRAY

BACKGROUND

The invention relates generally to tissue micro array processing and imaging.

Tissue micro arrays (TMA) are used for many analytic and diagnostic purposes, one of which is to diagnose diseased tissue at the molecular level. Whatever the purpose, tissue micro arrays, on which tissue samples are fixed, are typically stained with a morphological stain or biomarker and then analyzed manually with a microscope, or an image may be taken of the TMA to retain the image for subsequent analysis or comparison. After the first stain is applied and imaged, one or more serial or successive stains or biomarkers may be applied and the TMA is analyzed again. The two or more serial images may then be compared. It has been an ongoing goal to automate this system while maintaining the quality and consistency of the analysis and resulting conclusions or data. Such efforts have proved to be less than optimal because of the inability to automate the analysis of the TMA after each serial stain is applied. Although systems exist that attempt to combine the serial images, these combined images result in inconsistent and inconclusive results because the serial images are merely co-registered based on the mechanical placement of the TMA on the imaging microscope. These combined images that are co-registered based solely on the mechanical location of the TMA fail to incorporate differences between the serial images including, but not limited to, mechanical misplacement, tissue distortion, autofluorescence, differing levels of focus when each image is taken, and anomalies associated with the curvature of the cells in the tissue sample.

Pathologists have used hematoxylin-eosin (H&E) staining for over a hundred years. Hematoxylin stains cell nuclei blue, while eosin, as a counter-stain, stains cytoplasm and connective tissue pink. In view of the long history of H&E use, well-established methods of use, and the large amount of data and publications relating to H&E use, there is a strong belief among many pathologists that H&E will continue to be the common practice over the next fifty years. However, more recently developed technologies, that use molecular biomarkers to obtain functional information and sub-cellular localization, have also proved to be valuable for diagnostics, prognosis and survival rates for various diseases.

H&E staining techniques are often favored because they are generally low cost, fast and efficient; the images are readily acquired and there exists a large body of knowledge and training about these techniques. On the other hand, molecular biomarkers can provide protein-associated pathways that are not visible with H&E techniques. More recently, immunohistochemistry (IHC) based image analysis algorithms were developed to quantify the localization of proteins in the tissue. The value of these more recent techniques generally exceeds the value of the H&E techniques in terms of survival rates, prognosis, population segmentation and drug response prediction. Nevertheless, due to the common use of H&E and the availability of data with known outcome and diagnosis associated with H&E, most image analysis and automated quantification techniques still rely primarily if not entirely on H&E data.

In instances in which H&E techniques and molecular biomarkers are used, the current pathological tissue imaging modalities involve either molecular labeling or traditional H&E labeling but not simultaneous labeling. Simultaneous labeling of both techniques is not used because of the auto-fluorescence characteristics of the H&E dyes. It is not possible to simultaneously image H&E dyes with molecular biomarker using current imaging techniques because of the auto-fluorescence characteristics of the H&E dyes. Chemical interactions of H&E dyes with the antibodies to which the molecular biomarkers are attached significantly limit the simultaneous imaging of H&E with biomarkers. As noted, although serial sections of H&E and fluorescent images have previously been serially compared, registration between such serial sections is poor because of tissue distortion and the optical and chemical effects of the stains.

BRIEF DESCRIPTION

Unlike previous methods, the sequential imaging and registration methods and system disclosed herein enable, for the first time, two or more markers to be presented digitally on the same tissue section. As noted, fluorescent markers were previously used alone to identify the nuclei, epithelia and stroma to provide information on the cell compartments. The methods combine the morphological function of fluorescent markers with the function of fluorescent biomarkers, which are used to identify the expression of proteins and pathways for disease in tissue, by sequential digitizing and processing the images based, in part, on cell morphology and biological pathways.

The sequential imaging and registration techniques described herein overlay the molecular image information with the color H&E images, which increases the number of information channels and the value of the resulting information derived from the multi-channel image. In one embodiment, the tissue is labeled with molecular biomarkers, and imaged through a fluorescence microscope, and then the tissue is re-labeled with H&E dyes, and imaged again, or vice versa. Then these images are aligned with image registration techniques, and different modalities are represented in the same coordinate system. Once the images are registered, image analysis techniques are greatly improved using the additional channels of information. For example, a multi-dimensional expectation maximization algorithm can detect different cell compartments from the registered multi-channel images. Based on the detected cell compartments, a mask of the tissue is created that differentiates the stroma from the epithelia and nuclei.

One or more of the methods generally comprises applying one or more molecular probes to bind to proteins that are over expressed in a disease such as cancer using an unstained tissue micro array (TMA). The TMA elements are imaged in a fluorescent microscope to measure the distribution of proteins in the tissue sample that are associated with a given disease state. The TMA is then stained with H&E or another appropriate morphological stain to show the morphology. The TMA is digitized and the image pixel are segmented into compartments based on clustering and detection algorithms. In one embodiment, the segmentation of the H&E stained color images generally comprises the steps of: separating the Red (R), Green (G) and Blue (B) channels and then measuring the color and intensity of the glands, epithelia, stroma and/or nuclei in a normal sample; computing the cluster centers in RGB space using the distance between each pixel and the cluster center; and refining the estimate for the cluster center by iterating the center estimate.

One embodiment of the method for automatically registering multi-channel images of a tissue micro array, generally comprises the steps of: providing a biological material on a substrate; applying one or more molecular probes, adapted to provide fluorescent molecular markers, to the biological material; obtaining a first digital image of the biological material and the fluorescent molecular markers; applying a morphological stain to the biological material; obtaining a second digital image of the biological material, computing information common to the first and second images; and co-registering the second image with the first image using one or more registration metrics. Registration metrics may include, but are not limited to, mean square error, cross-correlation, joint entropy, mutual information, normalized mutual information, sum of squared differences, and sum of absolute differences, as well as metrics that are based feature points such as center of nuclei, orientation of membrane structures can be defined to align the images.

The registration metric may comprise features computed from the images and/or raw pixel intensities. Such feature information may comprise nuclei, epithelia, stroma or any type of extracellular matrix material.

The method may further comprise the steps of segmenting at least one of the images into nuclei, epithelia and stroma; and creating a mask of the stroma. The method may also further comprise the step of identifying one or more molecular pathways based on the molecular marker, wherein the molecular pathway is indicative of a disease. Although the methods may be used for a variety of diseases, one type for which the method is particularly suited is cancer including, but not limited to, epithelial cancers such as but not limited to breast, prostate and colon cancers.

The method may also comprise the step of quantifying the identified molecular pathways as a function of one or more morphological structures selected from a group consisting of the segmented nuclei, epithelia and stroma.

The method is also adapted so that the images may be superimposed on each other using an interactive viewer. Still further the method may comprise the step of viewing one or more of the images with a virtual microscope for communication over a communications network.

Another embodiment of the method for automatically registering multi-channel images of a tissue micro array, generally comprises the steps of: providing a digital image of a biological material stained with one or more fluorescent molecular markers; providing a digital image of the biological material stained with one or more morphological stains; and co-registering the second image with the first image based on a one or more registration metrics.

The automated system for carrying out the method generally comprises: a means for at least temporarily storing the digital images stained with the molecular markers and the morphological stains; and a processor for co-registering the images using one or more registration metrics. The system may further comprise a means for displaying one or more of the images; an interactive viewer; a virtual microscope; and/or a means for transmitting one or more of the images over a communications network. The processor may also be adapted to segment the digital images into a plurality of morphological features; and to create a mask of one or more of the morphological features. The processor may also superimpose one or more of the images with each other based, at least in part, on the segmentation of the morphological features.

DRAWINGS

Figure 1B:
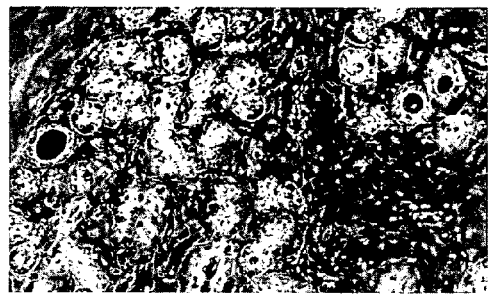
Figure 1C:
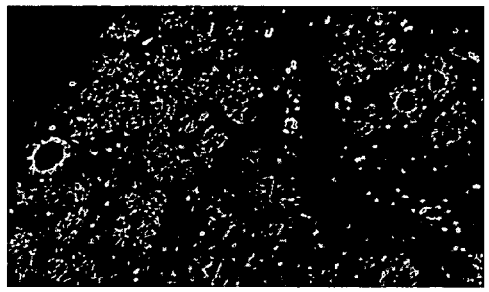
Figure 1D:
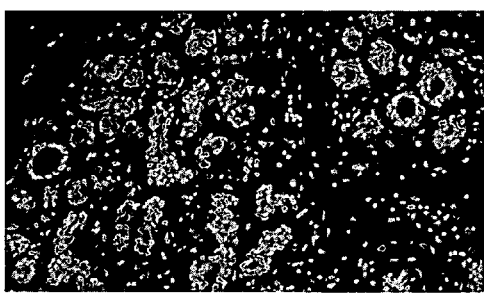
Figure 1E:
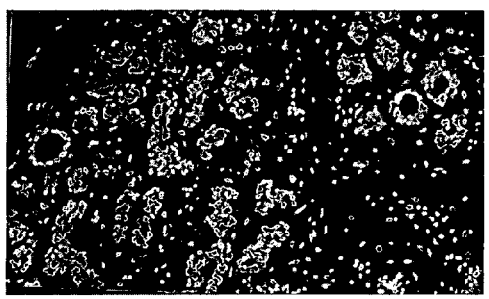
Figure 1F:
Figure 2A:
Figure 2B:
Figure 2C:
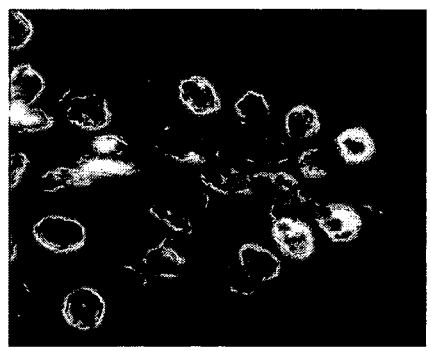
Figure 2D:
Figure 2E:
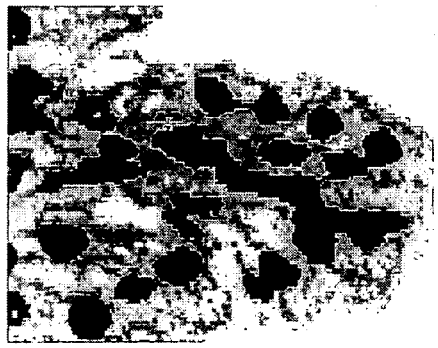
Figure 3:
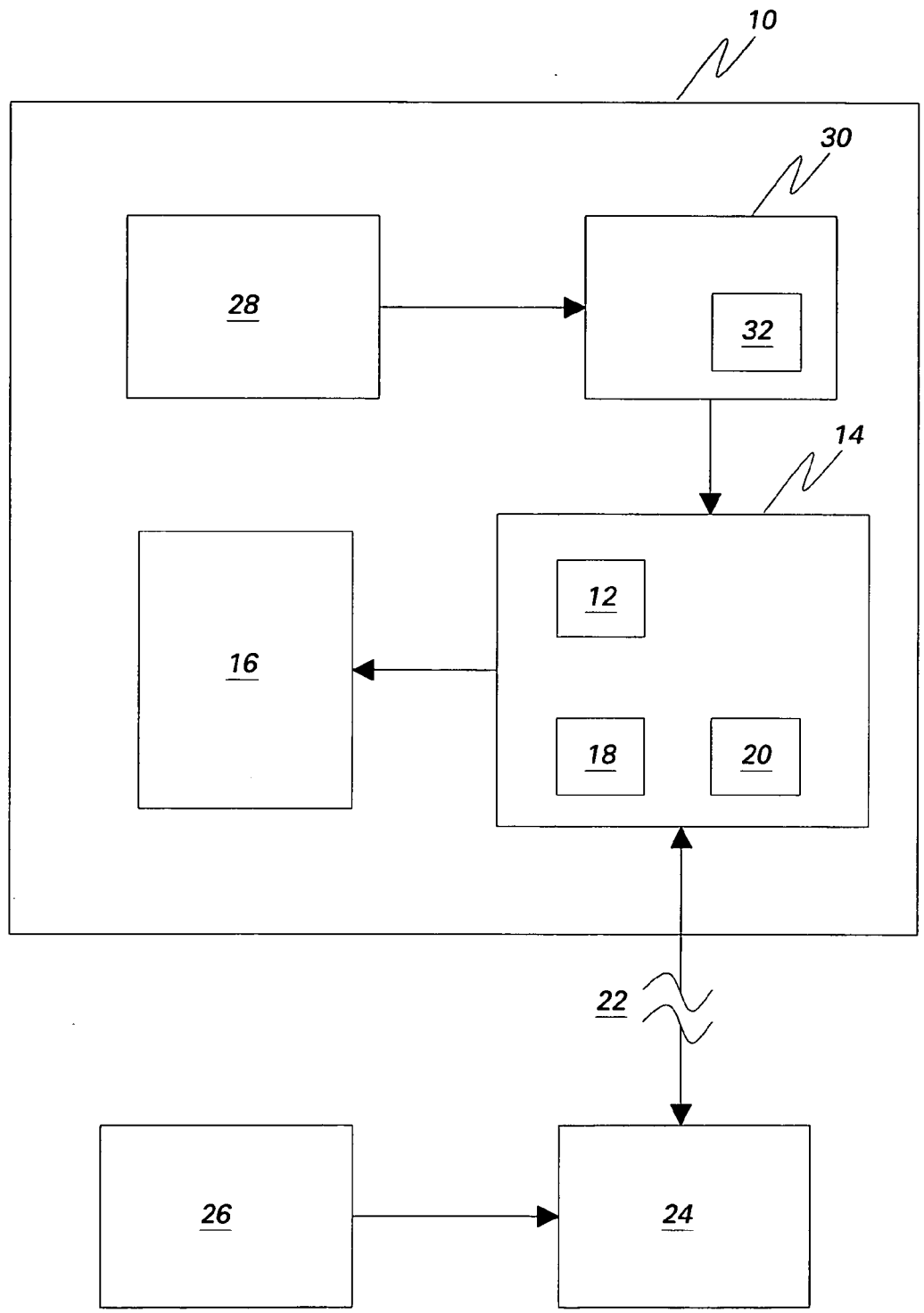
Figure 4:
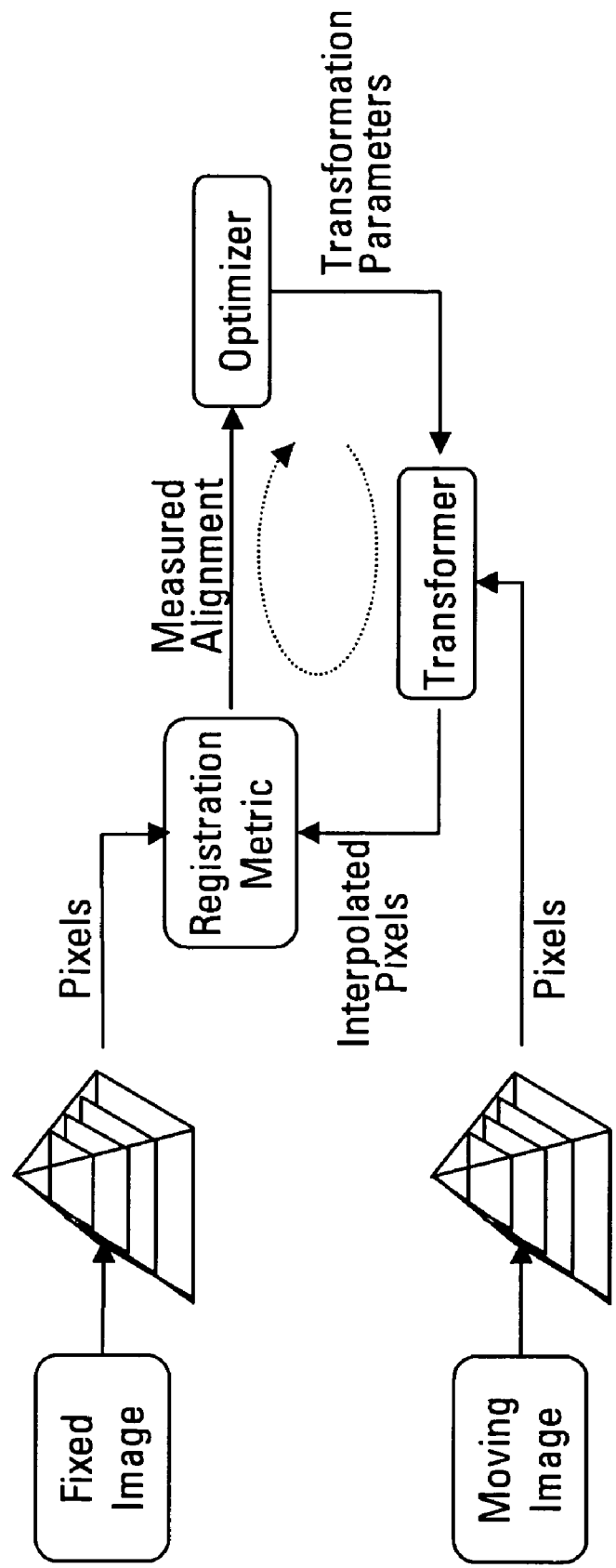

These and other features, aspects, and advantages of the present invention will become better understood when the following detailed description is read with reference to the accompanying drawings in which like characters represent like parts throughout the drawings, wherein:

FIG. 1A shows an embodiment of a three-channel (red, green, blue) color image of an H&E stained breast tissue section;
FIG. 1B shows the inverted intensity component of the H&E color image of FIG. 1A;
FIG. 1C shows a two-channel fluorescent image of the tissue in FIG. 1A stained with molecular biomarkers wherein green and blue colors are used to visualize the beta-catenin, and DAPI images, respectively;
FIG. 1D shows one of the components of the multiplexed biomarker image of FIG. 1C that has overlapping information with the H&E image of FIG. 1A;
FIG. 1E shows a registered DAPI image in the H&E coordinate system;
FIG. 1F shows the beta-catenin channel mapped into the H&E coordinate system using the registration parameters estimated from the DAPI and H&E images. Then the beta-catenin is superimposed with the H&E image, and shown in green color;
FIG. 2A shows an embodiment of an H&E image;
FIG. 2B shows the segmentation of the H&E image of FIG. 2A based on the three-color channels;
FIG. 2C shows a DAPI stained fluorescent image registered to the H&E image coordinate system;
FIG. 2D shows the segmentation of the single channel DAPI image;
FIG. 2E shows an embodiment of the segmentation result using all four channels simultaneously, the three channels from the H&E images and the registered DAPI channel wherein the segmentation results are presented with H&E-like false colors;
FIG. 3 is an embodiment of the system for co-registering multi-channel images of a tissue micro array; and
FIG. 4 is a schematic diagram of one of the preferred methods of the invention.

DETAILED DESCRIPTION

The preferred methods and preferred embodiments of system of the invention allow both molecular and morphological markers to be imaged from the same tissue sample using sequential imaging and co-registration techniques. Generally, the tissue, which is fixed or otherwise provided on a substrate such as, but not limited to, a TMA, a slide, a well, or a grid, is labeled with molecular biomarkers, and imaged through a fluorescent microscope. Then the tissue is re-labeled with one or more morphological stains such as H&E dyes, and imaged again. The methods are not limited to two images and can be adapted to co-register more than two images as needed. The images are overlaid using both hardware and software registration techniques, and the information is merged, whereby the technical effect is to co-register or otherwise produce multi-channel images. Every pixel in the multi-channel image represents both molecular and H&E information. This multi-channel registered image can be used for localizing tissue compartments by multi-dimensional segmentation algorithms. The pathologist may select regions of interest from the H&E images using a virtual microscope and then analyze the selected molecular florescence image. The molecular biomarkers advantageously provide functional and compartmental information that is not visible using H&E stains alone.

A variety of molecular biomarkers may be used such as fluorescent dyes bound to antibodies or proteins. Then the tissue is imaged under a fluorescent microscope using an excitation energy source that is tuned to the given biomarkers, and using various filters that are adapted to optimally collect the emitted light. Multiple biomarkers can be imaged simultaneously without moving the specimen under the microscope, or sequentially. For different biomarkers the excitation wavelength and the filters can be changed. Biomarkers may include, but are not limited to, the following list of markers which comprises a brief description of one or more but not necessarily all of the functions of each marker:

Her2/neu: epidermal growth factor over expressed in breast and stomach cancer, therapy by a monoclonal antibody slows tumor growth EGF-R/erbB: epidermal growth factor receptor ER: estrogen receptor required for growth of some breast cancer tumors, located in the nucleus and detected with ICH for deciding on therapy limiting estrogen in positive patients PR: progesterone receptor is a hormone that binds to DNA AR: androgen receptor is involved in androgen dependant tumor growth P53: tumor suppressor gene senses DNA damage is inactivated in 50% of human cancer β-catenin: oncogene in cancer translocates from the cell membrane to the nucleus, which functions in both cell adhesion and as a latent gene regulatory protein Phospho-β-Catenin: phosphorylated form of β-catenin degrades in the cytosol and does not translocate to the nucleus GSK3β: glycogen synthase kinase-3β protein in the Wnt pathway phosphorylates β-catenin marking the phospo-β-catenin for rapid degradation in the protosomes PKCβ: mediator G-protein coupled receptor NFKβ: nuclear factor kappa B marker for inflammation when translocated to the nucleus Bcl-2: B cell lymphoma oncogene 2 acts as an apoptosis inhibitor CyclinD: cell cycle control VEGF: vascular endothelial growth factor related to angiogenesis E-cadherin: cell to cell interaction molecule expressed on epithelial cells, the function is lost in epithelial cancers c-met: tyrosine kinase receptor.

At least one additional fluorescent morphological marker that carries a compartmental information is also included in this step. This marker is chosen such that it carries common information with the next step. This is essential to register the images.

Next, the tissue section is labeled with a morphological marker such as the traditional H&E dyes, and placed at the same location under the microscope. The location of the specimen under the microscope is controlled with electronic, magnetic, optical or mechanical sensors so that the specimen can be repeatedly located close to the same position for the next image acquisition. The microscope is designed such that it can acquire both bright field and fluorescent images. One such microscope may involve calibrated multiple optical paths and multiple cameras. After which, a bright field image of the tissue section is obtained using a digital camera. Due to positioning errors of the tissue slide, the pixel on the H&E image generally do not exactly overlay with the previous molecular image. To correct any such errors, the image registration techniques disclosed herein, such as the mutual information or correlation-based techniques, are used to register the two or more images and align them accurately. The registered image pairs of the examples described represent both molecular and H&E information for a given point on the tissue section. The two or more pairs can be combined as single multi-channel image, or they can be presented in multiple registered images. Morphological markers may include, but are not limited to, the following:

Keratin: marker for epithelial cells

Pan-cadherin: marker for the cell membrane

Smooth muscle actin: marker for muscle

DAPI: marker for the nucleus

Hematoxylin marker for DNA (blue stain)

Eosin: marker for cytoplasm depends on pH (red stain).

Some of these morhological markers can be imaged using a brightfield microscope, and some with fluorescent microscope. In any case, the morhological marker is chosen such that it has common information with the earlier step. For example if DAPI is used to image the nuclei in the earlier step, hematoxylin can be used to image the nuclei under a bright field microscope in the second step. Since they both stain the same compartment, the images can be alligned by image registration techniques.

As noted, the tissue was first labeled with one or more molecular biomarkers such as an IHC or one or more fluorescent dyes. Each of these dyes may have different characteristics, and may be binding to different compartments and proteins in the tissue. An example is the beta-catenin used in the embodiment described which highlights membrane-associated regions. Then the tissue is imaged under a fluorescent microscope with an appropriate excitation energy source tuned to a given biomarker and with filters appropriate for collecting the emitted light. Similarly, multiple biomarkers can be imaged simultaneously without moving the specimen under the microscope, or sequentially. As noted, the excitation wavelength and the filters can be changed for different markers.

Next, the tissue section is labeled using traditional H&E dyes or other appropriate morphological stains, and placed back under the microscope. Electronic, magnetic, optical or mechanical sensors control the location of the tissue section under the microscope so that the specimen can be repeatedly located in the same position for the next image acquisition. The microscope is designed so that it can acquire both bright field and fluorescent images. One such microscope may involve calibrated multiple optical paths and multiple cameras. A bright field image of the tissue section is obtained using a digital camera. Due to positioning errors of the tissue slide, the pixels on the H&E image may not exactly overlay with the previous molecular image. Image registration methods, such as mutual information or correlation-based methods are used to register the two images to align them accurately. The registered image pairs represent both molecular and H&E information for a given point on the tissue section. The two or more pairs can be combined as a single multi-channel image, or they can be presented in multiple registered images.

The number and types of stains used, and the sequence in which the morphological and biomarker stains are applied and imaged, is critical. Between the two sequential imaging steps, at least one pair of markers, such as DAPI and hematoxylin that carry the same compartmental information is used. These imaging techniques allow multi-channels of a variety of information to be analyzed from the same digital image. For example, the pathologists can look at the multi-channel image in the H&E mode to view the traditional H&E image, but they can also superimpose the overlaying molecular information by clicking a button on the computer screen.

The number of channels in the biomarker image is application specific, and based on how many compartments and protein associations are needed for the specific task. Usually three or four dyes can be easily applied simultaneously. There are some protein specific molecular biomarkers, such as beta-catenin that can bind to multiple compartments. If none of the desired biomarkers have any common compartmental information that can be used to register with the H&E images, an extra fluorescent nuclear marker is added so that the nuclear marker can be registered with nuclei stained with hematoxylin in the bright field images. For example, DAPI can be used as a nuclear stain, which emits blue fluorescence when bound to DNA and excited by UV light. Provided that there are common compartments/information between the H&E and the biomarker images, these methods can be applied to a broad class of biomarkers.

Co-registration is accomplished, in this example, using the mutual information from the various images. For example, an image of a TMA stained with DAPI and beta-catenin may be co-registered with images of the same TMA stained with H&E. This example combination of molecular and H&E stains is particular useful for epithelial tissue cancers such as breast, prostate and colon cancers.

The image registration algorithms may be grouped in two general categories, intensity-based and featured based. (FIG. 4) The feature extraction algorithms preferably utilize an initial image analysis and segmentation step. For pathology images, for example, the location, size, and shape of the nuclei can be extracted from both the H&E and DAPI images. Then this information is used to align the images using point-matching techniques. Features from epithelial tissue, muscle tissue, glands, and connective tissue or extracellular matrix may be extracted as well. Detection of the nucleus is relatively easier than other features due to geometric shape priors, however the difference between epithelial and muscle tissue is subtle, and both tissues do not always exist in the same tissue section. Intensity based registration does not typically utilize prior segmentation information and is applicable to a broad class of biomarkers.

The notation $I_F(x_F, y_F)$ is referred to herein as the fixed image to define the reference coordinate system, and the reference intensity values derived from the inverse of the luminance of the H&E color image. This inversion is optional if an information theoretic metric is used for registration. However, the inversion is needed when a correlation or mean-square error metric is used for registration. The notation $I_M(x_M, y_M)$ denotes the moving image, which, in this example, is the DAPI component of the multi-channel fluorescent image. The registration is the estimation of the underlying transformation parameters that maps the moving image into the fixed image coordinate system via minimizing a cost function, F;

$$\underset{\theta}{\mathrm{argmin}} F(I_F(x_F, y_F), I_M(T(x_M, y_M; \theta)))$$

where T represents spatial transformation with parameters $\theta$. More specifically, a similarity transform is used to incorporate translation, rotation, and scaling considerations. The translation and rotation is addressed to correct for any misplacement of the tissue slide, and the scaling is addressed to correct small focal plane changes. This transformation maps the moving image into the fixed image coordinate system;

$$T(x_M, y_M; \theta) \equiv \begin{bmatrix} \theta_1 & \theta_2 \\ -\theta_2 & \theta_1 \end{bmatrix} \begin{pmatrix} x_M \\ y_M \end{pmatrix} + \begin{pmatrix} \theta_3 \\ \theta_4 \end{pmatrix}.$$

Note that higher order transformation models, including but not limited to, affine, rigid, rigid+scaling, DCT-based, polynomial-based, spline-based, RBF-based, or higher order polynomial transformations, may also be used if desired such as, for example, instances in which geometric lens distortions are a concern.

A number of cost functions, including, but not limited to, mean-square-error, cross correlation, Kullback-Liebler distance, gradient difference metric, mutual information, normalized mutual information, sum of square differences, sum of absolute differences, and joint entropy may also be incorporated. Due to its robustness in registering multi modality images, the negative of the mutual information metric may be used and is defined as;

$$F(I_F(x_F, y_F), I_M(T(x_M, y_M; \theta))) = -H(I_F(x_F, y_F)) - H(I_M(T(x_M, y_M; \theta))) + H(I_F(x_F, y_F), I_M(T(x_M, y_M; \theta)))$$

where H represents the entropy of the image. The negation of this metric is due to the minimization process defined in the first equation.

As another example, after each tissue-processing step, the image pairs A and B are aligned by maximizing the mutual information I(A, B), which is expressed in terms of image entropy H(A, B) and individual image entropies. Entropy is related to the pixel intensity probability in each image $P_A$, $P_B$ and joint probability $P_{AB}$.

$$I(A, B) = H(A, B) - H(A) - H(B)$$

$$H(A) = -\Sigma P_A \ln(P_A)$$

$$H(B) = -\Sigma P_B \ln(P_B)$$

$$H(A, B) = -\Sigma P_{AB} \ln(P_{AB})$$

Both translation and a small rotation are applied with a multi-resolution search to find the maximum mutual information. Two unrelated images with a random pixel relationship $P_{AB} = P_A P_B$ will have zero mutual information. Image registration may be implemented with the open source toolkit (www.itk.org).

In one embodiment, the tissue goes through a multiplexing process in which the tissue is stained with DAPI and beta-catenin markers. A two-channel image is generated using a fluorescent microscope. FIG. 1C shows this two-channel fluorescent image of the image of FIG. 1A. In FIG. 1C green and blue colors are used to visualize the beta-catenin and DAPI images, respectively.

The channel that corresponds to DAPI (FIG. 1D) may be used as the registration channel because it represents common compartments, in this case the nuclei, with the H&E images. Then the tissue is stained with H&E dyes, and imaged with a bright-field microscope. This process results in a three-channel (red, green, blue) color image (FIG. 1A) of an H&E stained breast tissue section. The inverse of the luminance of this color image is calculated (FIG. 1B) as the intensity component of the H&E color image where the fixed image reference coordinate system is defined. The DAPI image is then registered and transformed into the fixed image coordinate system (FIG. 1E). The registration parameters estimated from the DAPI and H&E images are used to map the beta-catenin channel into the H&E coordinate system. Then beta-catenin is superimposed with the H&E image, and shown in green color (FIG. 1F). The order of staining and imaging with the biomarkers and then with the morphological stains is critical. The order of staining may be reversed or otherwise interchanged depending on the number and type of stains used and the imaging information desired.

FIG. 1D shows one of the components of the multiplexed biomarker image of FIG. 1C that has overlapping information with the H&E image of FIG. 1A. As noted, in this example, it is the DAPI channel that is later registered with the intensity image of the H&E.

Superimposing the molecular biomarker information on the H&E information provides a qualitative tool for the pathologist to view both modalities on the same tissue. This provides great diagnostic value since the pathways can now be easily superimposed on a standard H&E slide.

These imaging methods also provide greatly improved value to quantitative pathology. Image analysis algorithms can benefit from the added channels to separate the tissue compartments. FIGS. 2A and 2B show a three-channel H&E color image, and its segmented compartments using an unsupervised Expectation Maximization (EM) algorithm. A DAPI stained fluorescent image (acquired before the H&E staining) is registered to the H&E image, and transformed to H&E coordinate system (FIG. 2C). The DAPI-H&E image may be viewed as a four-channel single image (FIG. 2D). A four dimensional EM algorithm segments the compartments and the result is shown in FIG. 2E. As shown, the combined segmentation is greatly improved over the H&E segmentation alone or a single channel DAPI segmentation. The segmentation results shown in the Figures are presented with H&E like false colors.

Another embodiment of the method for automatically registering multi-channel images of a tissue micro array, generally comprises the steps of: providing a digital image of a biological material stained with one or more fluorescent molecular markers; providing a digital image of the biological material stained with one or more morphological stains; identifying mutual information in the first and second images; and co-registering the second image with the first image based on the mutual information.

The automated system 10 (FIG. 3) for carrying out the methods generally comprises: a means 12 for at least temporarily storing the digital images stained with the molecular markers and the morphological stains; and a processor 14 for identifying the mutual information, segmenting the objects, creating a mask of one or more of the objects, and co-registering the images. The means for storing may comprise any suitable hard drive memory associated with the processor such as the ROM (read only memory), RAM (random access memory) or DRAM (dynamic random access memory) of a CPU (central processing unit), or any suitable disk drive memory device such as a DVD or CD, or a zip drive or memory card. The means for storing may be remotely located from the processor or the means for displaying the images, and yet still be accessed through any suitable connection device or communications network including but not limited to local area networks, cable networks, satellite networks, and the Internet, regardless whether hard wired or wireless. The processor or CPU may comprise a microprocessor, microcontroller and a digital signal processor (DSP).

The means for storing 12 and the processor 14 may be incorporated as components of an analytical device such as an automated high-speed fluorescent system that images and analyzes TMAs in one system. An example of such a system is the IN Cell Analyzer 3000 (General Electric Healthcare Bio-Sciences Group, Piscataway, N.J.). As noted, system 10 may further comprise a means for displaying 16 one or more of the images; an interactive viewer 18; a virtual microscope 20; and/or a means for transmitting 22 one or more of the images or any related data or analytical information over a communications network 24 to one or more remote locations 26.

The means for displaying 16 may comprise any suitable device capable of displaying a digital image such as, but not limited to, devices that incorporate an LCD or CRT. The means for transmitting 22 may comprise any suitable means for transmitting digital information over a communications network including but not limited to hardwired or wireless digital communications systems. As in the IN Cell Analyzer 3000, the system may further comprise an automated device 28 for applying one or more of the stains and a digital imaging device 30 such as, but not limited to, a fluorescent imaging microscope comprising an excitation source 32 and capable of capturing digital images of the TMAs. Such imaging devices are preferably capable of auto focusing and then maintaining and tracking the focus feature as needed throughout the method.

The processor may also be adapted to segment the digital images into a plurality of morphological features; and to create a mask of one or more of the morphological features. The processor may also superimpose one or more of the images with each other based, at least in part, on the segmentation of the morphological features.

These methods merge molecular pathology and standard anatomical pathology. H&E based staining is the most common bright field microscopy staining technique used in standard pathology. As described above, hematoxylin stains cell nuclei blue, while, as a counter-stain, eosin stains cytoplasm and connective tissue pink. There are a great number of other known stain combinations that can be used as alternative staining for bright field microscopy. For example, Feulgen staining can be used to image nucleic acids, or Orcein can be used to image connective tissue fibers. As noted, the methods and system are not limited to H&E staining and can be used to superimpose any bright field microscopy images with fluorescent microscopy images as long as there is common information available between the microscopy modalities to register the images.

These multi-channel methods are not limited to morphological stains or fluorescent biomarkers or even to pathology. Any stain that enables some informative aspect or feature of a biological sample to be visualized so that it can be digitally imaged and processed would be suitable for these methods. Suitable stains include, but are not necessarily limited to, cytological or morphological stains, immunological stains such as immunohisto- and immunocyto-chemistry stains, cytogenetical stains, in situ hybridization stains, cytochemical stains, DNA and chromosome markers, and substrate binding assay stains. Other medical and bioscience applications can benefit from the extended multi-channels. These multi-channel methods provide a flexible framework in which markers can be imaged sequentially without being limited to optical, chemical, and biological interactions.

While only certain features of the invention have been illustrated and described herein, many modifications and changes will occur to those skilled in the art. It is, therefore, to be understood that the appended claims are intended to cover all such modifications and changes as fall within the scope and spirit of the invention.

The invention claimed is:

1. A method for registering images of a biological material, comprising the steps of;
   applying one or more molecular probes, adapted to provide fluorescent molecular markers, to said biological material;
   obtaining a digital image of said biological material and the fluorescent molecular markers;
   applying a morphological stain to said biological material;
   obtaining a digital image of said biological material; and
   aligning and combining digital images, one of which is a moving image and one of which is a fixed image, into a single digital image, that comprises the fluorescent markers and the morphological stain, whereby aligning the digital images comprises identifying a plurality of feature points of the biological material in the moving image and the fixed image, and aligning one or more pixels in the moving and fixed images that correspond to the identified feature points, wherein the feature points comprise a cellular structure, a subcellular structure, or proteins, or combinations thereof.

2. The method of claim 1, wherein one or more of said registration metrics comprises mutual information from the first and second images.

3. The method of claim 2, wherein one or more of said registration metrics comprises, at least in part, feature based information comprising one or more features selected from a group consisting of: nuclei, epithelia and stroma.

4. The method of claim 1, wherein said one or more of said registration metrics comprises, at least in part, intensity based information.

5. The method of claim 1, further comprising the step of segmenting at least one of said images into nuclei, epithelia and stroma.

6. The method of claim 1, further comprising the step of creating a digital mask of at least a portion of cellular stroma.

7. The method of claim 1, further comprising the step of identifying one or more molecular pathways based on said molecular markers.

8. The method of claim 7, wherein one or more of said molecular pathways is indicative of a disease.

9. The method of claim 8, wherein said disease is cancer.

10. The method of claim 9, wherein said cancer is an epithelial cancer.

11. The method of claim 1, further comprising the steps of, segmenting at least one of said images into nuclei, epithelia and stroma; and
identifying one or more molecular pathways based on said molecular markers.

12. The method of claim 11, further comprising the step of creating a digital mask of said stroma.

13. The method of claim 11, further comprising the step of quantifying one or more of said identified molecular pathways as a function of one or more morphological structures selected from a group consisting of said nuclei, epithelia and stroma.

14. The method of claim 1, further comprising the step of viewing one or more of said images with a virtual microscope for communication over a communications network.

15. The method of claim 1, wherein one or more of said registration metrics is selected from a group consisting of mean square error, joint entropy, mutual information from the first and second images, normalized mutual information from the first and second images, cross-correlation, sum of squared differences, and sum of absolute differences.

16. A system for carrying out the method of claim 1, comprising
a means for storing the digital images; and
a processor for co-registering said second image with said first image based on one or more registration metrics.

17. A method for registering images of a biological material, comprising the steps of,
providing a digital image of a biological material comprising one or more fluorescent molecular markers;
providing a digital image of said biological material comprising one or more morphological stains;
aligning and combining digital images, one of which is a moving image and one of which is a fixed image, into a single digital image using a processor, that comprises the fluorescent markers and the morphological stain, whereby aligning the digital images comprises identifying a plurality of feature points of the biological material in the moving image and the fixed image, and aligning one or more pixels in the moving and fixed images that correspond to the identified feature points, wherein the feature points comprise a cellular structure, a subcellular structure, or proteins, or combinations thereof; and
displaying one or more of the provided digital images or the single digital image on a display device.

18. A system for carrying out the method of claim 17, comprising;
a means for storing the digital images; and
a processor for co-registering said first and second images based on said information common to said first and second images.

19. The method of claim 17, wherein said information common to said first and second images comprises one or more types of feature based information selected from a group consisting of: nuclei, epithelia and stroma.

20. The method of claim 17, further comprising the steps of:
segmenting said digital images into a plurality of morphological features; and
creating a digital mask of one or more of said morphological features.

21. The method of claim 20, wherein one or more of said morphological features is selected from group consisting of: nuclei, epithelia, stroma, and extracellular matrix.

22. The method of claim 17, wherein said information common to said first and second images comprises intensity based information.

23. The method of claim 22, further comprising the steps of:
segmenting said digital images into a plurality of morphological features; and
creating a digital mask of one or more of said morphological features.

24. A method for registering images of a biological material, comprising the steps of;
applying one or more molecular probes, adapted to provide fluorescent molecular markers, to said biological material;
obtaining a first digital image of said biological material and the fluorescent molecular markers;
identifying one or more molecular pathways corresponding to said molecular markers;
applying a morphological stain to said biological material;
obtaining a second digital image of said biological material;
segmenting said second image to identify one or more morphological features; and
aligning and combining the digital images, one of which is a moving image and one of which is a fixed image, based, at least in part, on said step of segmenting said second image, whereby aligning the digital images comprises identifying a plurality of feature points of the biological material in the first and second images, and aligning one or more pixels in the first and second images that correspond to the identified feature points, wherein the feature points comprise a cellular structure, a subcellular structure, or proteins, or combinations thereof.

* * * * *